United States Patent
Iceman

(10) Patent No.: US 10,874,475 B2
(45) Date of Patent: Dec. 29, 2020

(54) ROBOTIC SURGICAL SYSTEMS AND METHODS FOR MONITORING APPLIED FORCES

(71) Applicant: Covidien LP, Mansfield, MA (US)

(72) Inventor: Jason Iceman, Cheshire, CT (US)

(73) Assignee: COVIDIEN LP, Mansfield, MA (US)

( * ) Notice: Subject to any disclaimer, the term of this patent is extended or adjusted under 35 U.S.C. 154(b) by 252 days.

(21) Appl. No.: 15/766,957

(22) PCT Filed: Nov. 10, 2016

(86) PCT No.: PCT/US2016/061221
§ 371 (c)(1),
(2) Date: Apr. 9, 2018

(87) PCT Pub. No.: WO2017/083453
PCT Pub. Date: May 18, 2017

(65) Prior Publication Data
US 2018/0296299 A1    Oct. 18, 2018

Related U.S. Application Data

(60) Provisional application No. 62/254,433, filed on Nov. 12, 2015.

(51) Int. Cl.
*A61B 90/00* (2016.01)
*A61B 50/13* (2016.01)
(Continued)

(52) U.S. Cl.
CPC .............. *A61B 90/06* (2016.02); *A61B 34/30* (2016.02); *A61B 34/35* (2016.02); *A61B 34/37* (2016.02);
(Continued)

(58) Field of Classification Search
CPC combination set(s) only.
See application file for complete search history.

(56) References Cited

U.S. PATENT DOCUMENTS 6,723,106 B1 * 4/2004 Charles ................. B25J 9/1065
606/130
8,716,973 B1    5/2014 Lammertse
(Continued)

FOREIGN PATENT DOCUMENTS

CN    101277657 A    10/2008
CN    104690711 A    6/2015
(Continued)

OTHER PUBLICATIONS

International Search Report & Written Opinion of Int'l Appln. PCT/US2016/061221 dated Feb. 22, 2017.
(Continued)

*Primary Examiner* — Abby Y Lin
*Assistant Examiner* — Renee LaRose
(74) *Attorney, Agent, or Firm* — Carter, DeLuca & Farrell LLP

(57) ABSTRACT

A robotic surgical system includes a robotic arm and a force detection system coupled to the robotic arm. The force detection system includes a sensor configured to detect a force being applied on a patient as the robotic arm is translated to a position relative to a patient.

14 Claims, 7 Drawing Sheets

(51) Int. Cl.
  *A61B 34/37*   (2016.01)
  *G01L 5/22*    (2006.01)
  *A61B 34/30*   (2016.01)
  *A61B 34/35*   (2016.01)

(52) U.S. Cl.
  CPC .............. *A61B 50/13* (2016.02); *G01L 5/226* (2013.01); *A61B 2090/064* (2016.02)

(56) References Cited

U.S. PATENT DOCUMENTS

| | | |
|---|---|---|
| 2004/0117094 A1 | 6/2004 | Colburn |
| 2005/0113971 A1 | 5/2005 | Zhang et al. |
| 2007/0156157 A1 | 7/2007 | Nahum et al. |
| 2009/0088639 A1 | 4/2009 | Maschke |
| 2009/0248038 A1* | 10/2009 | Blumenkranz ........ B25J 13/085 606/130 |
| 2010/0094312 A1 | 4/2010 | Ruiz Morales et al. |
| 2011/0106141 A1 | 5/2011 | Nakamura |
| 2011/0270443 A1 | 11/2011 | Kamiya et al. |
| 2012/0116416 A1 | 5/2012 | Neff et al. |
| 2014/0058564 A1 | 2/2014 | Zhao et al. |

FOREIGN PATENT DOCUMENTS

| | | |
|---|---|---|
| WO | 2007041267 A2 | 4/2007 |
| WO | 2015142802 A1 | 9/2015 |

OTHER PUBLICATIONS

Extended European Search Report dated Jun. 5, 2019 corresponding to counterpart Patent Application EP 16864960.6.
Chinese Office Action for application No. 201680065313.2 dated May 8, 2020 with English translation.

* cited by examiner

ROBOTIC SURGICAL SYSTEMS AND METHODS FOR MONITORING APPLIED FORCES

CROSS-REFERENCE TO RELATED APPLICATIONS

This application is a U.S. National Stage Application filed under 35 U.S.C. § 371(a) of International Patent Application Serial No. PCT/US2016/061221, filed Nov. 10, 2016, which claims the benefit of and priority to U.S. Provisional Patent Application Ser. No. 62/254,433, filed Nov. 12, 2015, the entire disclosure of which is incorporated by reference herein.

BACKGROUND

Robotic surgical systems are used in minimally invasive medical procedures because of their increased accuracy and expediency relative to handheld surgical instruments. In these robotic surgical systems, a robotic arm supports a surgical instrument having an end effector mounted thereto by a wrist assembly. In operation, the robotic arm is moved to a position over a patient and then guides the surgical instrument into a small incision via a surgical port or a natural orifice of a patient to position the end effector at a work site within a patient's body.

The height of the robotic arm over a patient may need to be adjusted (i.e., the robotic arm is lowered) to precisely position the end effector at a work site within a patient's body. During this process, the robotic arm and/or the surgical instrument attached thereto may exert a downward force on the anatomy, e.g., an abdominal wall of a patient.

Accordingly, it would be useful to be able to monitor and/or control the movement of the robotic arm relative to the anatomy of a patient and the force applied thereon.

SUMMARY

In accordance with an embodiment of the present disclosure, a robotic surgical system is provided. The robotic surgical system includes a robotic arm and a force detection system coupled to the robotic arm. The force detection system includes a sensor configured to detect a force being applied to a patient as the robotic arm is translated to a position relative to a patient.

In some embodiments, the robotic surgical system may include a control device in communication with the sensor of the force detection system. The control device may be configured to change the position of the robotic arm relative to a patient when the force being detected by the sensor exceeds a predetermined force threshold.

It is contemplated that the force detection system may further include a base plate and a top plate pivotably coupled to the base plate. The sensor may be disposed between the base plate and the top plate.

It is envisioned that the force detection system may further include a pivoting member disposed between the base plate and the top plate.

In some aspects of the present disclosure, the sensor may include a top portion and a bottom portion. The top portion of the sensor may be coupled to the top plate and the bottom portion of the sensor may be coupled to the base plate.

In some embodiments, the top plate may include a first end and a second end. The robotic arm may be located adjacent to the first end of the top plate.

It is contemplated that the base plate may include a first end and a second end. The sensor may be located between and coupled to the base plate and the top plate at the second end of the top plate and the second end of the base plate.

It is envisioned that the top plate may include a top surface and a bottom surface. The robotic arm may be coupled to the top surface of the top plate.

In some aspects of the present disclosure, the robotic surgical system may further include a cart base. The cart base may include a vertical column having the force detection system supported thereon and a plurality of casters coupled to the vertical column. The plurality of casters may be configured to enable movement of the cart base.

In some embodiments, the vertical column may have an adjustable height to change a height of the robotic arm relative to a patient.

It is contemplated that the robotic surgical system may further include a surgical instrument attached to an end of the robotic arm.

It is envisioned that the sensor may be a strain gauge load cell, a piezoelectric load cell, a hydraulic load cell, a pneumatic load cell, or an optical load cell.

In another aspect of the present disclosure, a method of monitoring a force being applied on a patient is provided. The method includes applying a force on a patient with a robotic arm, determining the force applied on the patient using a sensor coupled to the robotic arm, comparing the determined force applied on the patient with a predetermined force threshold, and adjusting a position of the robotic arm relative to the patient if the determined force applied on the patient exceeds the predetermined force threshold.

In some embodiments, applying the force on the patient with the robotic arm may include engaging the patient with a surgical instrument that is coupled to the robotic arm.

It is contemplated that adjusting the robotic arm relative to the patient may include disengaging the surgical instrument from the patient if the force applied exceeds the predetermined force threshold.

It is envisioned that determining the force applied on the patient may include measuring a tension load on the sensor resulting from a pivoting of a top plate that supports the robotic arm thereon relative to a base plate, wherein the sensor may be disposed between the top plate and the base plate.

In some aspects of the present disclosure, the method may further include communicating the determined force applied on the patient to a control device. The control device may then compare the determined force applied on the patient with the predetermined force threshold.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
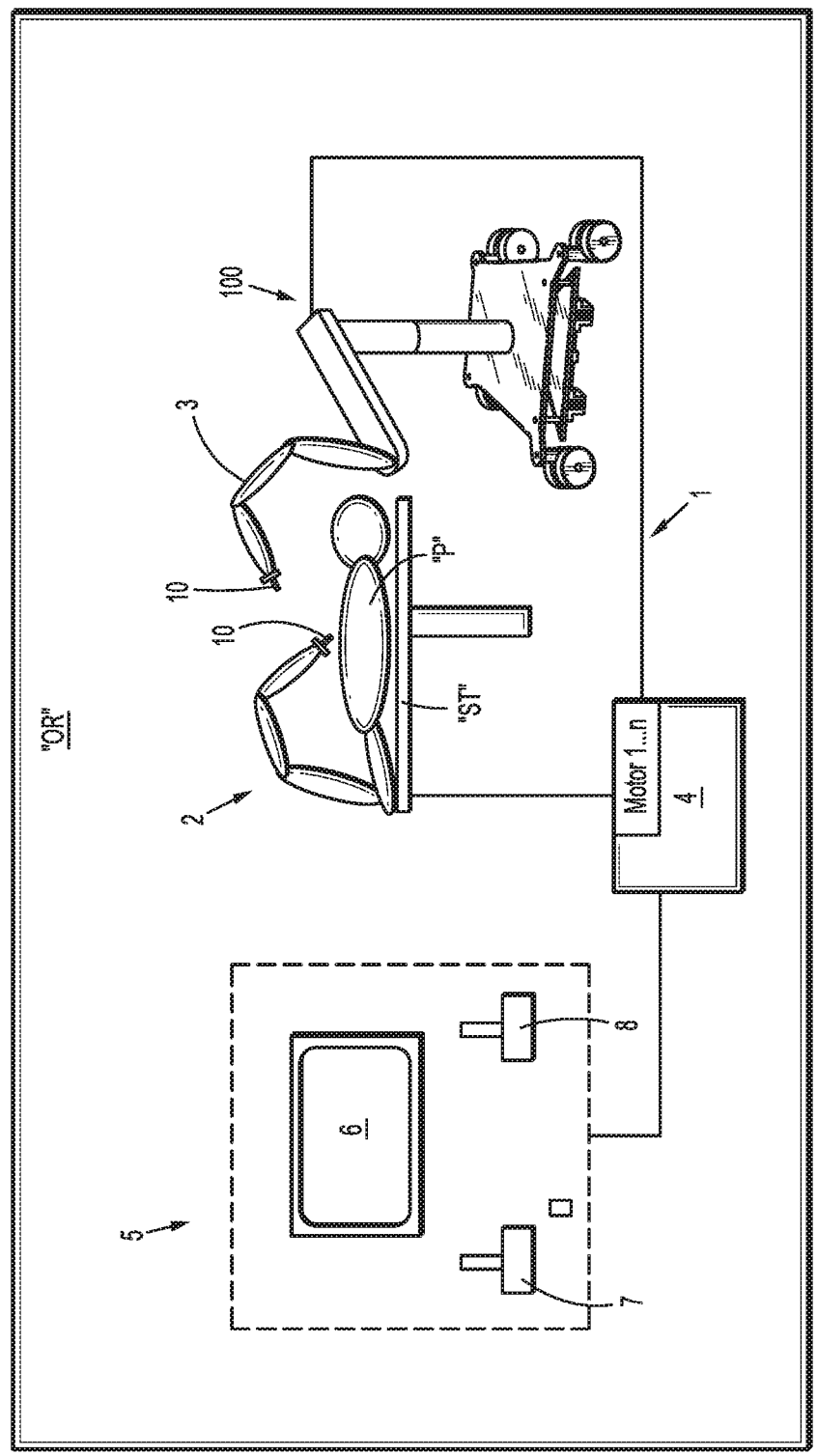
FIG. 1 is a schematic illustration of a robotic surgical system including a surgical cart assembly in accordance with the present disclosure.

Embodiments of the presently disclosed robotic surgical system for monitoring applied force and methods of use thereof are described in detail with reference to the drawings, in which like reference numerals designate identical or corresponding elements in each of the several views. As used herein the term "distal" refers to that portion of the robotic surgical system or component thereof, that is closest to the patient, while the term "proximal" refers to that portion of the robotic surgical system or component thereof, that is farthest from the patient.

As will be described in detail below, provided is a force detection system configured to monitor and measure a force being applied on the anatomy of a patient by a robotic arm and/or a surgical instrument coupled to the robotic arm. Additionally, provided is a control device configured to determine whether a force being applied on the anatomy of a patient by a robotic arm and/or a surgical instrument coupled thereto exceeds a patient specific predetermined force threshold and communicate a signal to the robotic arm to adjust the positioning thereof accordingly.

Referring initially to FIG. 1, a surgical system, such as, for example, a robotic surgical system 1 is shown. In embodiments, robotic surgical system 1 is located in an operating room "OR." Robotic surgical system 1 generally includes a plurality of surgical robotic arms 2, 3 having a surgical instrument, such as, for example, an electromechanical instrument 10 removably attached thereto; a control device 4; and an operating console 5 coupled with control device 4.

Operating console 5 includes a display device 6, which is set up in particular to display three-dimensional images; and manual input devices 7, 8, by means of which a person (not shown), e.g., a surgeon, is able to telemanipulate robotic arms 2, 3 in a first operating mode, as known in principle to a person skilled in the art. Each of the robotic arms 2, 3 may be composed of a plurality of members, which are connected through joints.

Robotic arms 2, 3 may be driven by electric drives (not shown) that are connected to control device 4. Control device 4 (e.g., a computer) is set up to activate the drives, in particular by means of a computer program, in such a way that robotic arms 2, 3 and thus electromechanical instrument 10 (including the electromechanical end effector (not shown)) execute a desired movement according to a movement defined by means of manual input devices 7, 8. Control device 4 may also be set up in such a way that it regulates the movement of robotic arms 2, 3 and/or of the drives.

Robotic surgical system 1 is configured for use on a patient "P" lying on a surgical table "ST" to be treated in a minimally invasive manner by means of a surgical instrument, e.g., electromechanical instrument 10. Robotic surgical system 1 may also include more than two robotic arms 2, 3, the additional robotic arms likewise being connected to control device 4 and being telemanipulatable by means of operating console 5. A surgical instrument, for example, electromechanical instrument 10 (including the electromechanical end effector), may also be attached to the additional robotic arm.

The robotic arms, such as for example, robotic arm 3, is supported on a surgical cart assembly 100. Surgical cart assembly 100 may incorporate control device 4. In embodiments, the robotic arms, such as for example, robotic arm 2 may be coupled to the surgical table "ST."

For a detailed discussion of the construction and operation of a robotic surgical system, reference may be made to U.S. Patent Application Publication No. 2012/0116416, filed on Nov. 3, 2011, entitled "Medical Workstation," the entire contents of which are incorporated herein by reference.

Figure 2A:
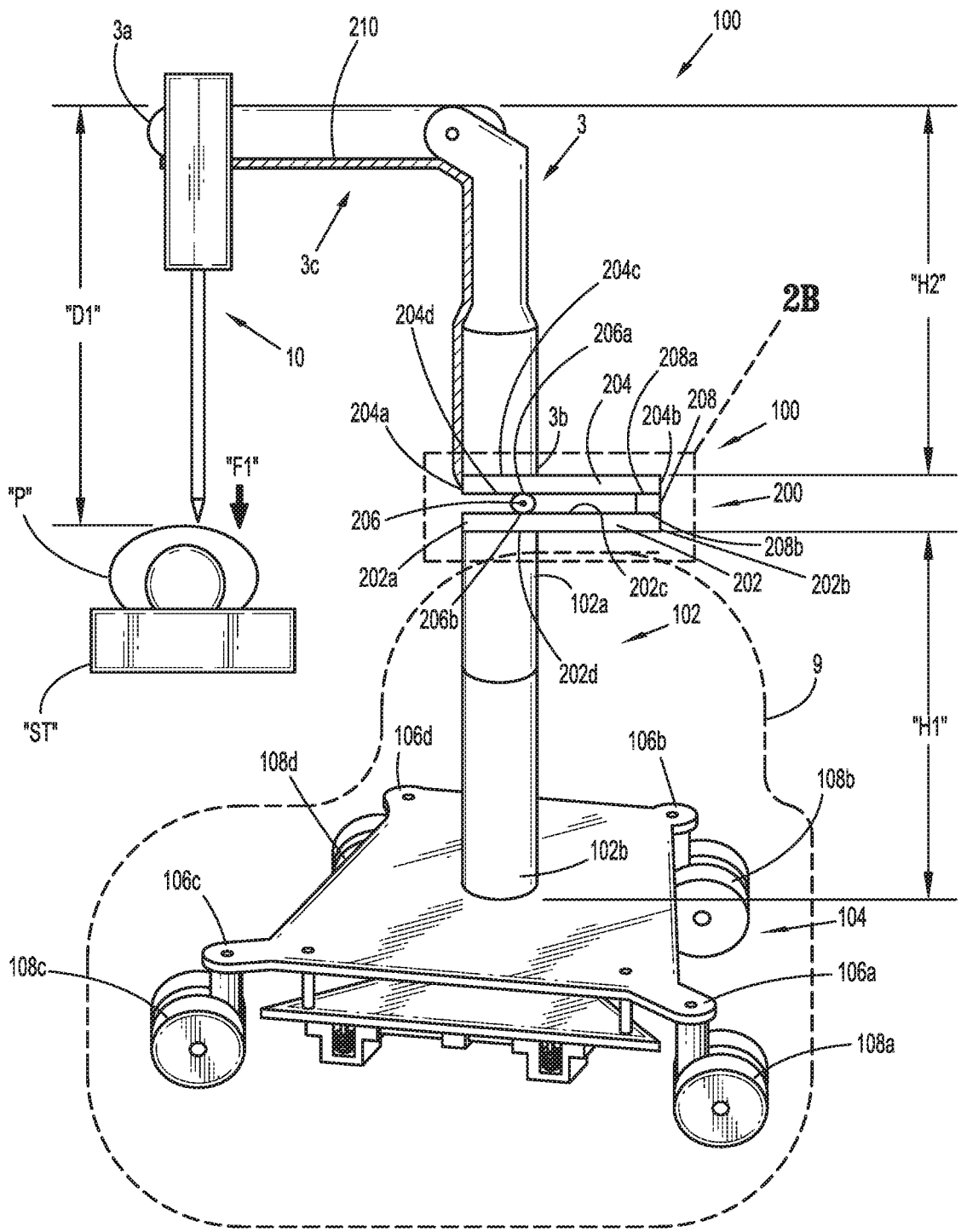
FIG. 2A is a perspective view of the surgical cart assembly of FIG. 1 having a force detection system in accordance with the present disclosure.

With reference to FIG. 2A, one exemplary embodiment of a surgical cart assembly of robotic surgical system 1 configured for use in accordance with the present disclosure is shown generally using reference numeral 100. Surgical cart assembly 100 is configured to move robotic arm 3 to a selected position within operating room "OR" (FIG. 1) and to detect and control a force "F1" applied by robotic arm 3 on a patient "P," as will be described in detail below. Surgical cart assembly 100 generally includes robotic arm 3, electromechanical instrument 10, which is attached to robotic arm 3, a cart base 9 configured for supporting robotic arm 3 thereon, and a force detection assembly 200 disposed between robotic arm 3 and cart base 9.

Cart base 9 of surgical cart assembly 100 includes a vertical column 102 and a platform 104 that supports vertical column 102 thereon. Vertical column 102 has a first end 102a and a second end 102b and defines a height "H1" of vertical column 102 therebetween. Vertical column 102 is telescopic such that height "H1" of vertical column 102 may be selectively adjusted. In embodiments, vertical column 102 includes a motor (not shown) configured to adjust height "H1" thereof.

Platform 104 is fixed to second end 102b of vertical column 102 and includes four flanges 106a, 106b, 106c, and 106d, having respective casters 108a, 108b, 108c, and 108d (shown in phantom) attached thereto. In some embodiments, platform 104 may include more than four flanges and casters or fewer than four flanges and casters. Further, in some embodiments, platform 104 may be detachably coupled to second end 102b of vertical column 102.

Figure 2B:
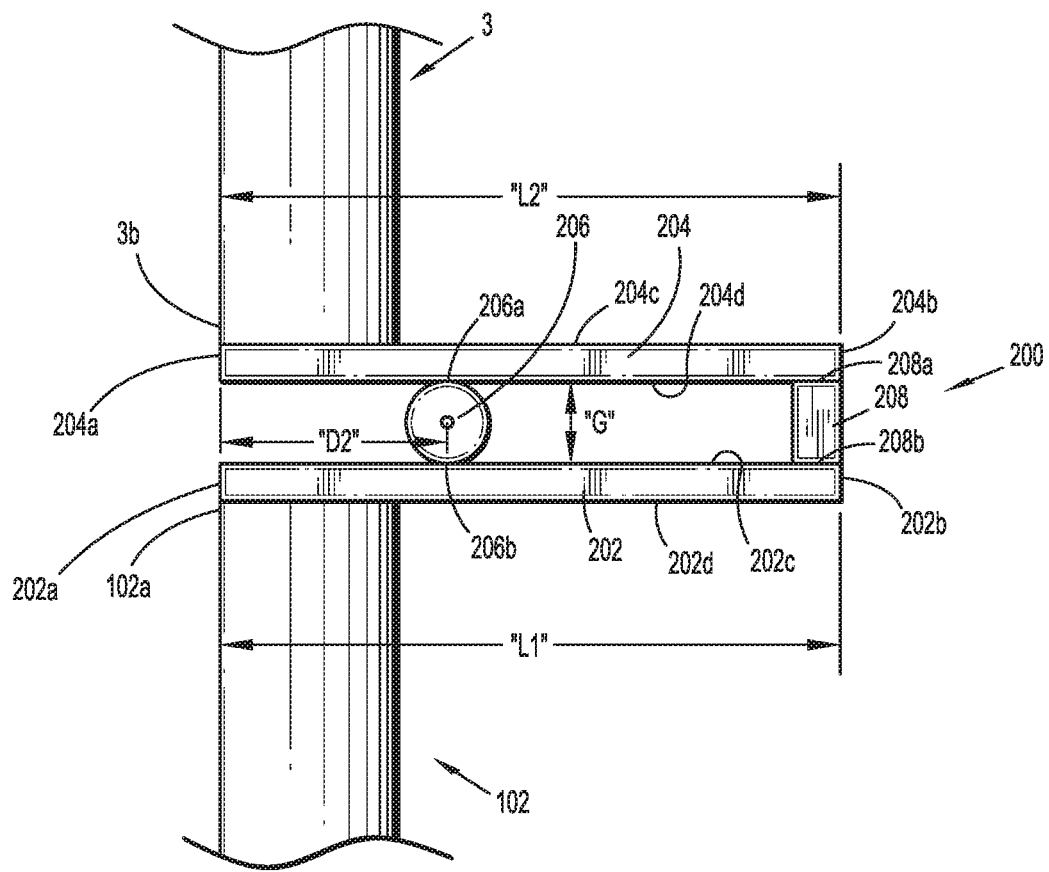
FIG. 2B is an enlarged, side view of the area of detail labeled "2B" show in FIG. 2A illustrating the force detection system.

With reference to FIGS. 2A and 2B, force detection system 200 of surgical cart assembly 100 is configured to sense or detect force "F1" applied by electromechanical instrument 10 on a surface, for example, patient "P." Force detection system 200 is interposed between an end 3b of robotic arm 3 and cart base 9. In some embodiments, instead of force detection system 200 being incorporated into surgical cart assembly 100, force detection assembly 200 may be interposed between robotic arm 2 and surgical table "ST."

Height "H1" of vertical column 102 may be adjusted (e.g., vertical column 102 may be telescopic as noted above) to correspondingly adjust a distance "D1" between an end 3a of robotic arm 3 and patient "P." Alternately, in some embodiments, distance "D1" between end 3a of robotic arm 3 and patient "P" may be adjusted by adjusting a height "H2" between ends 3a, 3b of robotic arm 3 (e.g., robotic arm 3 may be telescopic). In either variation, it is contemplated that robotic arm 3 and/or electromechanical instrument 10 may apply force "F1" on patient "P" upon engaging the anatomy of patient "P." As such, force detection system 200 is configured to detect and measure force "F1" by measuring a resulting equal and opposing force "F2" being applied on robotic arm 3 and/or electromechanical instrument 10 by the anatomy of patient "P."

Force detection system 200 includes a base plate 202, a top plate 204, and a pivot member 206 that pivotably couples base plate 202 and top plate 204 to one another. Base plate 202 includes a first end 202a and a second end 202b, wherein ends 202a, 202b define a length "L1" of base plate 202 therebetween. Similarly, top plate 204 includes a first end 204a and a second end 204b, wherein ends 204a, 204b define a length "L2" of top plate 204 therebetween. In embodiments, length "L1" of base plate 202 is equal to length "L2" of top plate 204. Alternately, in some embodiments, length "L1" of base plate 202 may be greater than or less than length "L2" of top plate 204.

Further, base plate 202 includes a top surface 202c and a bottom surface 202d. Similarly, top plate 204 includes a top surface 204c and a bottom surface 204d. In embodiments, surfaces 202c, 202d, 204c, and 204d of plates 202, 204, respectively, are planar. As illustrated in FIG. 2B, bottom surface 204d of top plate 204 and top surface 202c of base plate 202 define a gap distance "G" therebetween to space apart base plate 202 and top plate 204. As such, base plate 202 and top plate 204 are parallel to one another when no force "F1" is being applied to patient "P." Base plate 202 and top plate 204 are rectangular shaped. However, in some embodiments, base plate 202 and top plate 204 may assume a variety of shapes, such as, for example, squared, circular, triangular, or the like.

Robotic arm 3 is supported on top surface 204c of top plate 204. Specifically, second end 3b of robotic arm 3 is coupled to top surface 204c of top plate 204 at the first end 204a thereof. However, in some embodiments, robotic arm 3 may be located on alternative positions along length "L2" of top plate 204. In some embodiments, second end 3b of robotic arm 3 is fixedly coupled to top surface 204c of top plate 204. Alternatively, in some embodiments, second end 3b of robotic arm 3 may be detachably coupled to top surface 204c of top plate 204.

Pivot member 206 is disposed between base plate 202 and top plate 204 to allow top plate 204 to pivot relative to base plate 202. Pivot member 206 may be a hinge, a cylindrical member, or a rectangular member. However, in some embodiments, suitable alternatives for pivot member 206 are also contemplated. Pivot member 206 includes a top portion 206a and a bottom portion 206b. As noted above, pivot member 206 pivotably couples base plate 202 and top plate 204. Specifically, top portion 206a of pivot member 206 is coupled to bottom surface 204d of top plate 204 and bottom portion 206b of pivot member 206 is coupled to top surface 202c of base plate 202. In embodiments, portions 206a, 206b of pivot member 206 are fixedly coupled to surfaces 204d, 202c of plates 204, 202, respectively. However, in some embodiments, portions 206a, 206b of pivot member 206 may be detachably coupled to surfaces 204d, 202c of plates 204, 202, respectively.

Pivot member 206 is disposed between top plate 204 and base plate 202 near the respective first ends 204a and 202a thereof. However, it is contemplated that pivot member 206 may be disposed at various locations between length "L2" of top plate 204 and length "L1" of base plate 202. A distance "D2" is defined between pivot member 206 and first end 204a of top plate 204. It is contemplated that distance "D2" between pivot member 206 and first end 204a of top plate 204 may be stored in a memory device (not shown) in control device 4 and used in the calculation for determining force "F1" imparted by robotic arm 3 and/or electromechanical instrument 10 on a patient "P" (FIG. 1).

With continued reference to FIGS. 2A and 2B, force detection system 200 also includes a load cell or sensor 208 configured to sense when top plate 204 pivots relative to base plate 202 to ultimately determine the force "F1" imparted by robotic arm 3 and/or electromechanical instrument 10 on a patient "P" (FIG. 2A). Sensor 208 is located between and coupled to base plate 202 and top plate 204 at respective second ends 202b, 204b thereof. However, it is contemplated that sensor 208 may be disposed at various locations between length "L2" of top plate 204 and length "L1" of base plate 202. Sensor 208 includes a top portion 208a and a bottom portion 208b. Top portion 208a of sensor 208 is coupled to bottom surface 204d of top plate 204 and bottom portion 208b of sensor 208 is coupled to top surface 202c of base plate 202. Portions 208a, 208b of sensor 208 are fixedly coupled to surfaces 204d, 202c of plates 204, 202, respectively. However, in some embodiments, portions 208a, 208b of sensor 208 may be detachably coupled to surfaces 204d, 202c of plates 204, 202, respectively.

Various configurations of sensor 208 are possible and within the purview of the present disclosure. For example, in embodiments, sensor 208 may be a strain gauge load cell, a piezoelectric load cell, a hydraulic load cell, a pneumatic load cell, or an optical load cell. However, for the purpose of brevity, the features of sensor 208 disclosed herein will be directed towards a strain gauge load cell configured to measure a tension load between base plate 202 and top plate 204 as second ends 202b, 204b of the respective plates 202, 204 are approximated such that sensor 208 is compressed therebetween.

Sensor 208 includes a transducer (not shown), which converts a load "L" into a measurable electrical output, i.e., a signal readable by control device 4. Specifically, sensor 208 is configured to measure a change in load "ΔL" between base plate 202 and top plate 204 as top plate 204 rotates in a direction indicated by arrow "C" (see FIG. 3C) about pivot member 206 with respect to base plate 202 when robotic arm 3 and/or electromechanical instrument 10 engages and imparts force "F1" on the anatomy of patient "P."

Robotic arm 3 includes another sensor 210 configured to sense when electromechanical instrument 10 makes contact with a fixed surface, for example, tissue of a patient "P." Specifically, robotic arm 3 has a patient facing surface 3c between ends 3a, 3b thereof, wherein surface 3c includes sensor 210. In some embodiments, sensor 210 may be operably coupled to electromechanical instrument 10 such that contact between electromechanical instrument 10 and patient "P" is detected by sensor 210. In use, as distance "D1" between first end 3a of robotic arm 3 and patient "P" is adjusted, sensor 210 detects when there is contact between robotic arm 3 and/or electromechanical instrument 10 and patient "P." Upon contact, sensor 210 is configured to communicate a signal "S3" (see FIG. 3B) to control device 4, which initiates a calculation of force "F1" being exerted by robotic arm 3 and/or electromechanical instrument 10 on the anatomy of patient "P."

Figure 3A:
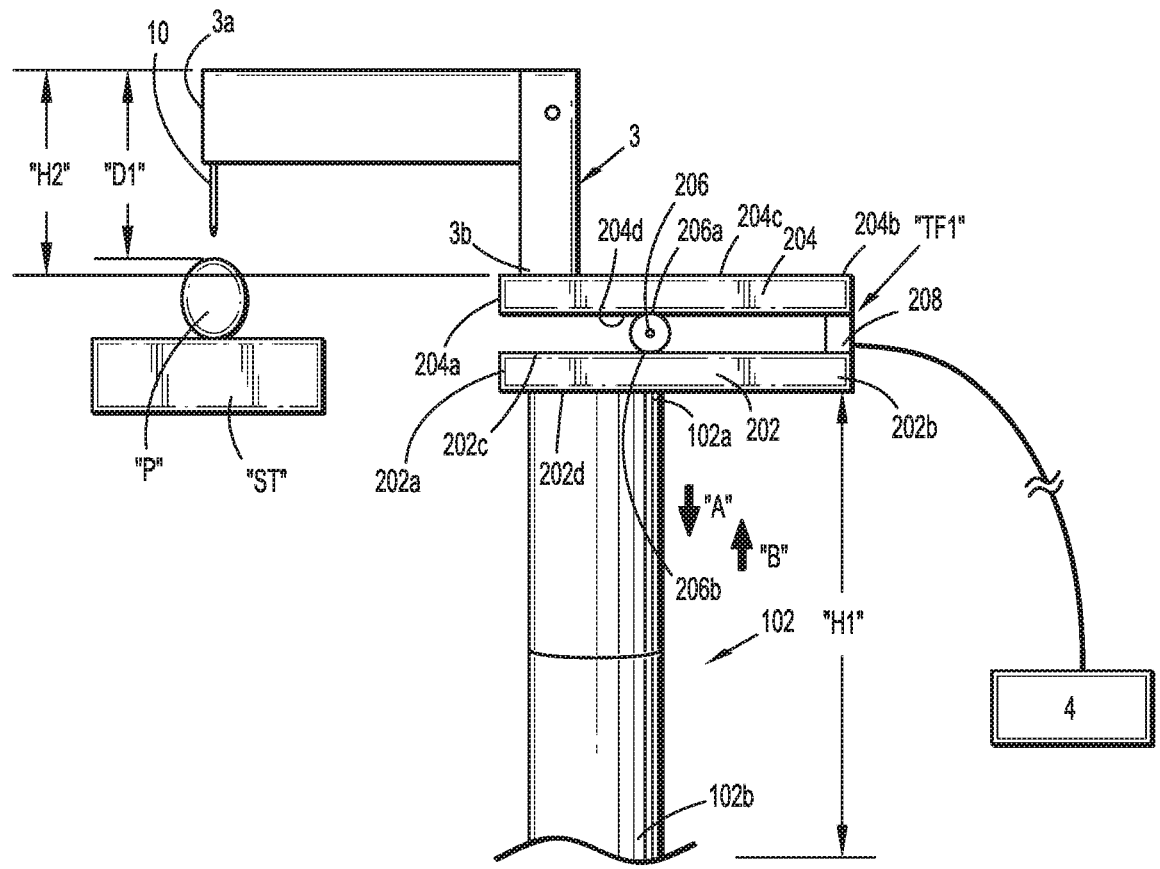
FIG. 3A is an enlarged, side view of the surgical cart assembly of FIG. 2A illustrating the force detection system in a first position.

In operation, with reference to FIG. 3A, robotic arm 3 is positioned adjacent patient "P" on surgical table "ST" such that first end 3a of robotic arm 3 is spaced apart from patient "P" by distance "D1." In this initial position, vertical column 102 of cart base assembly 100 has height "H1" and robotic arm 3 has height "H2." With electromechanical instrument 10 spaced from patient "P," sensor 208 of force detection system 200 measures a starting tension load "TL1" between base plate 202 and top plate 204.

Figure 3B:
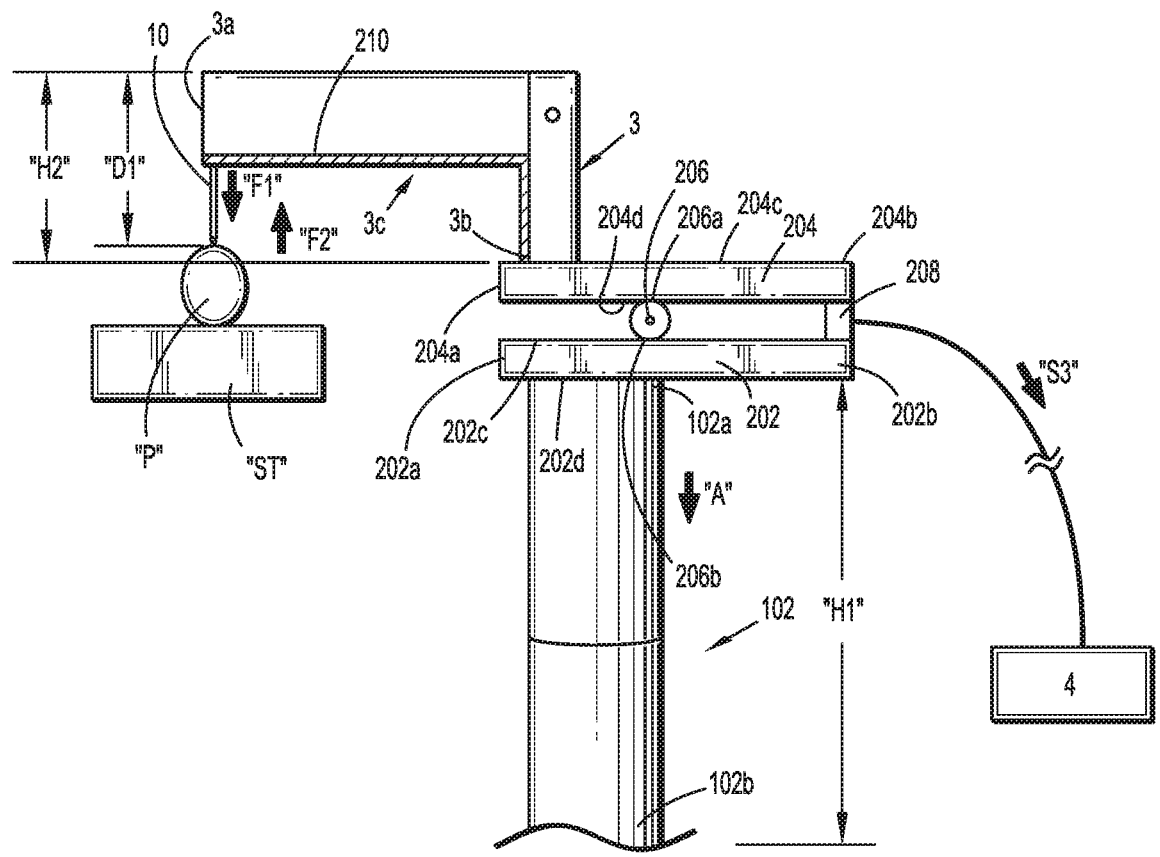
FIG. 3B is an enlarged, side view of the surgical cart assembly of FIG. 2A illustrating the force detection system in a second position.

With reference to FIG. 3B, in order to access a surgical site (not shown) on or within patient "P," distance "D1" between first end 3a of robotic arm 3 and patient "P" is adjusted by adjusting height "H1" of vertical column 102 or height "H2" of robotic arm 3 (using a motor, not shown), in a direction indicated by arrow "A" in FIG. 3B. The continued movement of robotic arm 3 and electromechanical instrument 10 ultimately results in electromechanical instrument 10 engaging patient "P," which exerts force "F1" on the anatomy thereof. As a result, the anatomy of patient "P" exerts an equal and opposing force "F2" on robotic arm 3 and/or electromechanical instrument 10. In embodiments in which sensor 210 of robotic arm 3 is employed, sensor 210 senses that a distal end of electromechanical instrument 10 has contacted patient "P," and communicates signal "S3" to control device 4 to initiate the calculation of force "F1" and whether force "F1" exceeds a predetermine force "PF" threshold.

Figure 3C:
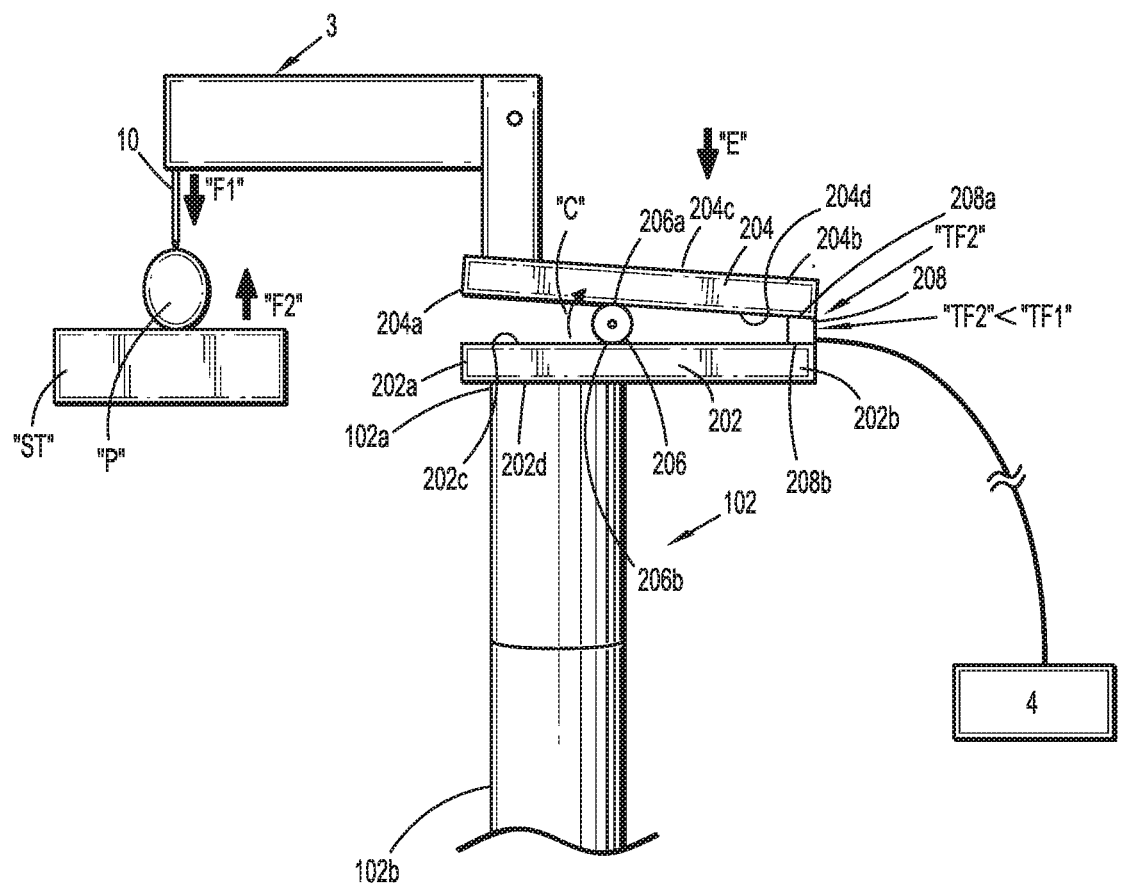
FIG. 3C is an enlarged, side view of the surgical cart assembly of FIG. 2A illustrating the force detection system in a third position.

With reference to FIG. 3C, force "F2" imparted by patient "P" on robotic arm 3 and/or electromechanical instrument 10 causes top plate 204 of force detection system 200 to rotate about pivot member 206 relative to base plate 202 in a direction indicated by arrow "C." As a result, second ends 202b, 204b of the respective plates 202, 204 are approximated thereby compressing portions 208a, 208b of sensor 208. Upon sensor 208 being compressed, the tension in sensor 208 is decreased from starting tension load "TL1." Sensor 208 measures a final tension load "TL2," wherein final tension load "TL2" is less than starting tension load "TL1."

Figure 3D:
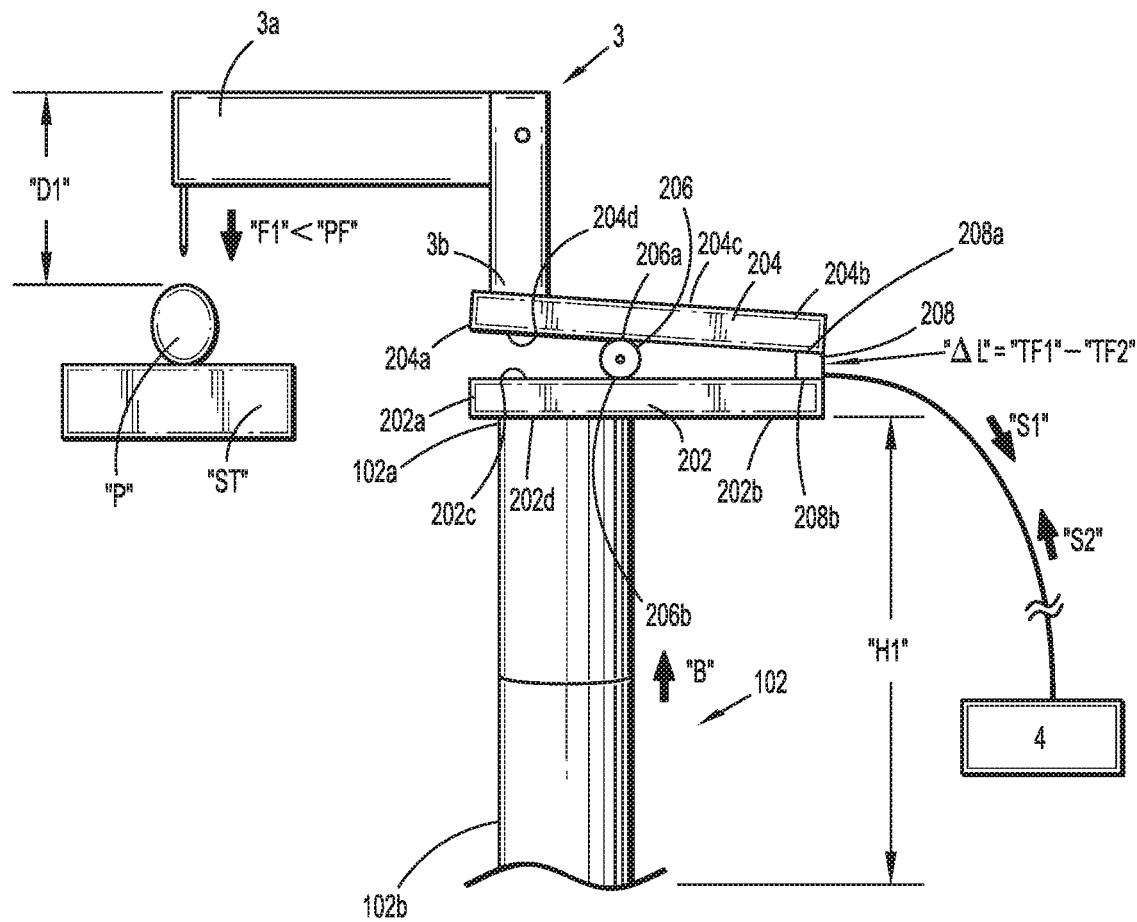
FIG. 3D is an enlarged, side view of the surgical cart assembly of FIG. 2A illustrating the force detection system in a fourth position.

With reference to FIG. 3D, sensor 208 communicates a signal "S1" to control device 4 including the measured change in load "ΔL," i.e., "TL1"-"TL2" between base plate 202 and top plate 204. Using this data, control device 4 calculates force "F1" being exerted by robotic arm 3 and/or electromechanical instrument 10 on the anatomy of patient "P" and determines whether force "F1" exceeds predetermined force "PF" threshold. The predetermined force "PF" threshold may be calculated based on data relating to patient "P" stored in control device 4, e.g., age, height, weight, etc., of patient "P," to determine the maximum amount of force "F1" that the anatomy of patient "P" can safely withstand without injury. If force "F1" exceeds the predetermined force "PF" threshold, control device 4 sends signal "S2" to robotic arm 3 and/or electromechanical instrument 10 to disengage from patient "P." In some embodiments, signal "S2" from control device 4 may also initiate an auditory or visual alarm to warn medical personnel.

To disengage robotic arm 3 and/or electromechanical instrument 10 from patient "P," height "H1" of vertical column 102 or height "H2" of robotic arm 3 is increased to translate first end 102a of vertical column 102 or first end 3a of robotic arm 3 in the direction indicated by arrow "B," such that distance "D1" between first end 3a of robotic arm 3 and patient "P" is correspondingly increased. Upon disengaging electromechanical instrument 10 from patient "P," force "F1" applied on patient "P" is reduced to a force that is below the predetermined force "PF" threshold. In some embodiments, instead of increasing distance "D1" between first end 3a of robotic arm 3 and patient "P" upon control device 4 determining that force "F1" exceeds predetermined force "PF" threshold, control device 4 may stop all movement of electromechanical instrument 10.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the claimed invention. Therefore, the above description should not be construed as limiting, but merely as exemplifications of particular embodiments. Those skilled in the art will envision other modifications within the scope and spirit of the claims appended hereto.

What is claimed is:

1. A robotic surgical system, comprising:
    a robotic arm; and
    a force detection system coupled to the robotic arm, the force detection system including:
        a base plate having a first and second end portion;
        a top plate having a first and second end portion;
        a pivoting member disposed between the first end portions of the base plate and the top plate and configured to pivotably couple the top plate and the base plate; and
        a sensor disposed between the second end portions of the base plate and the top plate and configured to detect a force being applied to a patient as the robotic arm is translated to a position relative to a patient based on the top plate pivoting relative to the base plate.

2. The robotic surgical system of claim 1, further comprising a control device in communication with the sensor of the force detection system, the control device configured to change the position of the robotic arm relative to a patient when the force being detected by the sensor exceeds a predetermined force threshold.

3. The robotic surgical system of claim 1, wherein the sensor has a top portion and a bottom portion, wherein the top portion of the sensor is coupled to the top plate and the bottom portion of the sensor is coupled to the base plate.

4. The robotic surgical system of claim 1, wherein the robotic arm being located adjacent the first end of the top plate.

5. The robotic surgical system of claim 1, wherein the top plate has a top surface and a bottom surface, the robotic arm being coupled to the top surface of the top plate.

6. The robotic surgical system of claim 1, further comprising a cart base including:
    a vertical column having the force detection system supported thereon; and
    a plurality of casters coupled to the vertical column, the plurality of casters configured to enable movement of the cart base.

7. The robotic surgical system of claim 6, wherein the vertical column has an adjustable height to change a height of the robotic arm relative to a patient.

8. The robotic surgical system of claim 1, further comprising a surgical instrument attached to an end of the robotic arm.

9. The robotic surgical system of claim 1, wherein the sensor is a strain gauge load cell, a piezoelectric load cell, a hydraulic load cell, a pneumatic load cell, or an optical load cell.

10. A method of monitoring a force being applied on a patient, the method comprising:
    applying a force on a patient with a robotic arm;
    determining the force applied on the patient using a sensor disposed between second end portions of a base plate and a top plate, the base plate and top plate pivotably coupled at first end portions of the base plate and top plate, the sensor coupled to the robotic arm;
    comparing the determined force applied on the patient with a predetermined force threshold; and adjusting a position of the robotic arm relative to the patient if the determined force applied on the patient exceeds the predetermined force threshold.

11. The method of claim 10, wherein applying the force on the patient with the robotic arm includes engaging the patient with a surgical instrument that is coupled to the robotic arm.

12. The method of claim 11, wherein adjusting the robotic arm relative to the patient includes disengaging the surgical instrument from the patient if the force applied exceeds the predetermined force threshold.

13. The method of claim 10, wherein determining the force applied on the patient includes measuring a tension load on the sensor resulting from the pivoting of the top plate that supports the robotic arm thereon relative to the base plate.

14. The method of claim 10, further comprising communicating the determined force applied on the patient to a control device, wherein the control device compares the determined force applied on the patient with the predetermined force threshold.

\* \* \* \* \*